United States Patent
Shin et al.

(10) Patent No.: US 9,737,583 B2
(45) Date of Patent: Aug. 22, 2017

(54) COMPOSITION FOR PREVENTION OR TREATMENT OF ACUTE RENAL FAILURE INCLUDING HERBAL EXTRACT OR FRACTION THEREOF AS ACTIVE INGREDIENT

(71) Applicant: KOREA INSTITUTE OF ORIENTAL MEDICINE, Daejeon (KR)

(72) Inventors: Hyun Kyoo Shin, Daejeon (KR); Ju Young Jung, Daejeon (KR); Hye Kyung Ha, Seoul (KR); Chang Seob Seo, Daejeon (KR); Young Jung Kim, Gwangju (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 75 days.

(21) Appl. No.: 14/440,689

(22) PCT Filed: Nov. 6, 2013

(86) PCT No.: PCT/KR2013/010018
§ 371 (c)(1),
(2) Date: May 5, 2015

(87) PCT Pub. No.: WO2014/073855
PCT Pub. Date: May 15, 2014

(65) Prior Publication Data
US 2015/0335699 A1    Nov. 26, 2015

(30) Foreign Application Priority Data
Nov. 8, 2012 (KR) .................. 10-2012-0126355

(51) Int. Cl.
*A61K 36/9068* (2006.01)
*A61K 36/9064* (2006.01)

(52) U.S. Cl.
CPC ...... *A61K 36/9064* (2013.01); *A61K 2236/33* (2013.01); *A61K 2236/39* (2013.01)

(58) Field of Classification Search
CPC .................................... A61K 36/9068
USPC .................................. 424/756, 777
See application file for complete search history.

(56) References Cited

FOREIGN PATENT DOCUMENTS

| CN | 101053641 A | * | 10/2007 |
|----|-------------|---|---------|
| JP | 09-087190 | | 3/1997 |
| KR | 10-2002-0015906 | | 3/2002 |
| KR | 2002-0089081 | | 11/2002 |
| KR | 10-2004-0037396 | | 5/2004 |
| KR | 10-0646574 | | 11/2006 |
| KR | 20100005868 A | * | 1/2010 |
| KR | 10-2010-0092570 | | 8/2010 |
| KR | 10-2012-0111765 | | 10/2012 |

OTHER PUBLICATIONS

"Uses of Alcohol", http://www.chemguide.co.uk/organicprops/alcohols/uses.html.*
Hwang, J.-T. et al, "Isolation and Identification of antifungal compounds from Amomum cardamomun LINNE", International Symposium and KIPS, Fall Conference, Abstract PB-14, p. 152, 2010.

* cited by examiner

*Primary Examiner* — Chris R Tate
*Assistant Examiner* — Deborah Davis
(74) *Attorney, Agent, or Firm* — Parker Highlander PLLC

(57) ABSTRACT

The present invention relates to a composition including an Amomi Rotundus Fructus extract or a fraction thereof as an active ingredient, which can be used for the prevention, amelioration, or treatment of acute renal failure.

9 Claims, 16 Drawing Sheets

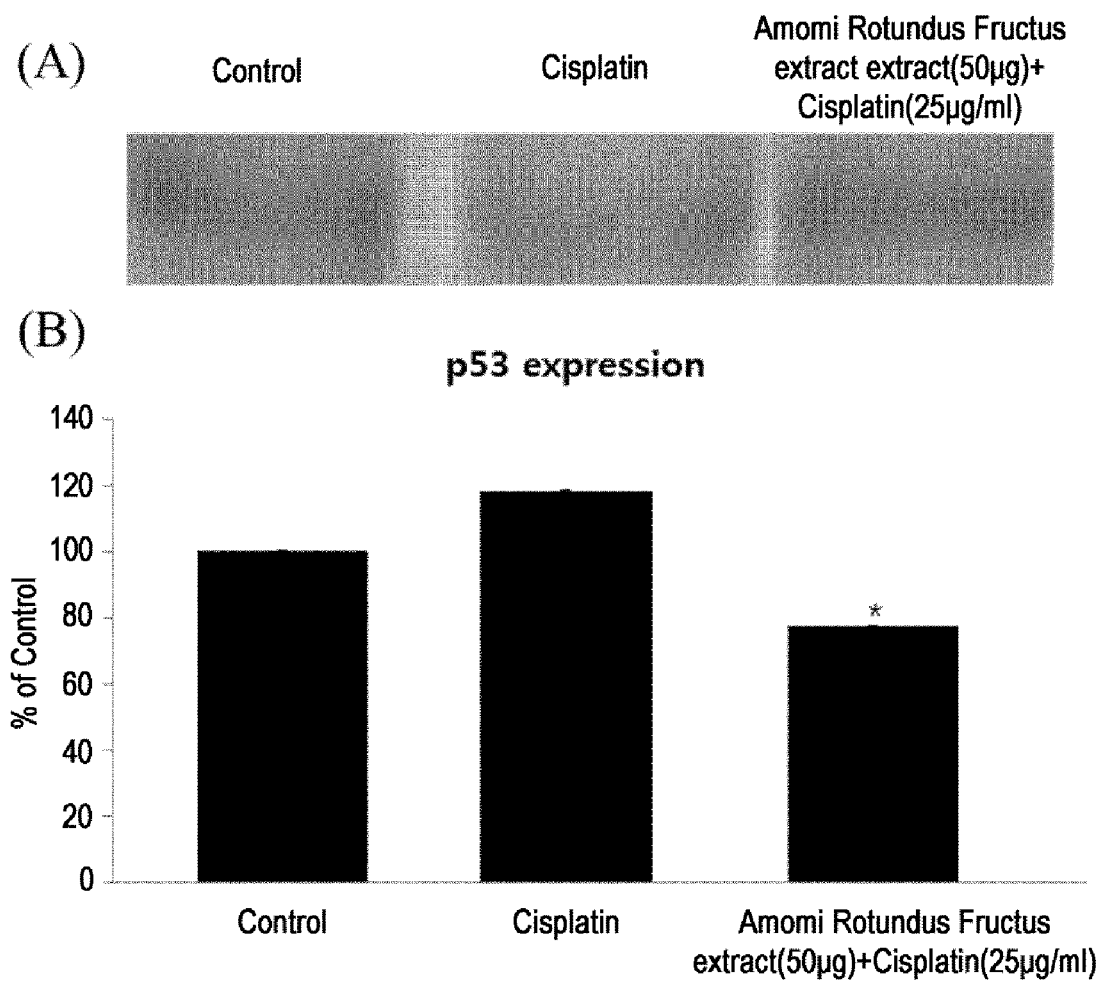
FIGS. 6A-B

COMPOSITION FOR PREVENTION OR TREATMENT OF ACUTE RENAL FAILURE INCLUDING HERBAL EXTRACT OR FRACTION THEREOF AS ACTIVE INGREDIENT

The present application is a national phase application under 35 U.S.C. §371 of International Application No. PCT/KR2013/010018, filed Nov. 6, 2013, which claims benefit of priority to Korean Application No. 10-2012-0126355, filed Nov. 8, 2012, the entire contents of each of the applications being hereby incorporated by reference.

BACKGROUND OF THE INVENTION

1. Field of the Invention

The present invention relates to a pharmaceutical composition or a functional food composition for the prevention, amelioration or treatment of acute renal failure, including an Amomi Rotundus Fructus extract or a fraction thereof as an active ingredient.

2. Description of the Related Art

Acute renal failure is a clinical syndrome characterized by rapid decline in renal functions, which is caused by a number of factors such as a reduction in renal blood flow, glomerulonephritis, and use of nephrotoxic antibiotics and anticancer agents. The acute renal failure is accompanied by a reduction in glomerular filtration rate (GFR) and urine output, azotemia caused by retention of nitrogenous waste products, perturbations in fluid and electrolyte balance, etc. Renal impairment in acute renal failure is associated with a high risk of 50% mortality, because it is difficult to restore the function if the cause is not managed and early treatment fails.

Particularly, azotemia, also called uremia, in acute renal failure is caused by the acute loss of renal function due to damage to renal tubules or reduction in GFR. A healthy adult must excrete a minimum of about 400 ml of urine each day to eliminate waste from the body through the kidneys. Urine output of less than 400 ml per day may indicate loss of kidney function.

The cause of acute renal failure can be largely divided into three categories on the basis of the kidney: pre-renal acute renal failure caused by inadequate blood circulation to the kidneys, intrinsic acute renal failure caused by damage to the kidney itself, and post-renal acute renal failure caused by an obstruction which can occur at any point of the urinary tract from the renal tubules to urethra. The symptoms of acute renal failure are caused by reduced blood flow to the kidneys, such as profound dehydration, excessive bleeding, burns, severe vomiting, diarrhea, long-term use of diuretics, pancreatitis and peritonitis, sepsis, and increased sodium excretion by the kidney, and this status is called pre-renal acute renal failure. In addition, direct damage to the kidney due to disease or renal toxic substance may cause changes in renal parenchyma, and this status is called intrinsic acute renal failure. Diseases corresponding to intrinsic acute renal failure include glomerulonephritis, renal vasculitis, long-lasting systemic renal failure or drug-induced acute renal tubular necrosis, thrombosis, external injury, atherosclerosis, and tumors in the kidneys.

As described above, there are many factors that cause acute renal failure. However, renal failure is caused not by only one factor but by complex actions or interactions between different factors. Further, acute renal failure shows a variety of physical signs. In some cases, acute renal failure has no symptoms but shows abnormal findings in laboratory tests. The symptoms involve low urine output, but not in all cases, poor appetite, nausea and vomiting, asterixis, edema, hypertension. In advanced stages, it develops dyspnea, seizures, and coma, leading to death in the most severe case.

The pathophysiology of cisplatin-induced acute renal failure has not been fully understood yet, but it is reported that the mechanisms of anticancer drugs, together with environmental factors, are involved. Exogenous cisplatin-induced acute renal failure that accounts for most of acute renal failure is attributed to absorption of cisplatin by urinary tubular cells in the kidneys.

Recently, it was reported that efficacies of natural substance on acute renal failure can be assessed by measuring changes in ROS (Reactive Oxygen Species), GSH (Glutathione) and p53 (El-Sayed el-S M et al. 2008, Takako Yokozawa, et al 2000). In particular, it is common that levels of ROS, GSH and p53 inducing and worsening symptoms are measured in the severity test of acute renal failure.

Of them, the ROS production level is known as a biochemical index associated with renal injury in various pathological conditions, and ROS-induced DNA damage leads to p53 activation. For this reason, high levels of ROS generally indicate the presence of renal disease. Further, increased GSH content indicates a cell-protecting effect, that is, a defense effect. In cisplatin-induced acute renal failure, the levels of ROS and GSH are changed. This change has been used as a basic index for diagnosing cisplatin-induced acute renal failure.

Meanwhile, it was known that p53 expression levels are increased in cisplatin-induced acute renal failure, and p53 expression is suppressed when therapeutic effects on acute renal failure occur.

Cisplatin (cis-diaminedichloroplatinum II) used to induce acute renal failure is one of the anticancer drugs frequently used, and it induces acute renal failure due to structural abnormalities of renal tubules. Free radicals are known to play an important role in cisplatin-induced renal tubule damage. Cisplatin-induced nephrotoxicity is also associated with an increase in lipid peroxidation in the kidney. It was reported that cisplatin itself prevents antioxidant effect in the kidney and reduces the level of GSH showing antioxidant effect in the kidney.

On the other hand, Amomi Rotundus Fructus is, as a fruit of *Amomum cadamomum* Linne belonging to the family Zingiberaceae, one of the herbal drugs used in oriental medicine, and commonly used for the treatment of diseases of the digestive system. Amomi Rotundus Fructus resolves dampness in the body, warms the body, activates the flow of energy, and stops vomiting. Further, Amomi Rotundus Fructus is known to promote the secretion of gastric juice and intestinal peristalsis, to inhibit the abnormal fermentation in intestines and to expel accumulated gas to enhance the appetite, and to be effective for indigestion or dyspepsia, and stomachache, belching, or vomiting due to chronic gastritis. Amomi Rotundus Fructus also has the functions of preventing hangovers, eliminating dampness in the spleen and stomach, invigorating the stomach, and promoting digestion. It also exhibits efficacies on tympanites and poor appetite, and vomiting due to cold stomach, stomachache, vomiting in pregnancy, or belching. Conventionally, with respect to the efficacies of Amomi Rotundus Fructus, Korean Patent Publication No. 10-2004-0037396 discloses a natural essential oil composition including Amomi Rotundus Fructus for the prevention or treatment of inflammatory diseases by aroma therapy, and a preparation method thereof, and Korean Patent Publication No. 10-2002-0089081 discloses a composition for the eradication of *Helicobacter pylori* including Amomi Rotundus Fructus.

However, none of the above documents disclose effects of an Amomi Rotundus Fructus extract or a fraction thereof on nephrotoxicity, particularly, acute renal failure.

Accordingly, the present inventors have made many efforts to develop a therapeutic agent for acute renal failure, which exhibits fewer side-effects and more excellent effects as a natural substance. As a result, they found that the Amomi Rotundus Fructus extract or the fraction thereof exhibits the effects of inhibiting ROS generation, increasing GSH levels, and reducing p53 expression in an acute renal failure cell model and thus it can be used as a composition for the prevention and treatment of acute renal failure, thereby completing the present invention.

SUMMARY OF THE INVENTION

An object of the present invention is to provide a pharmaceutical composition for the prevention or treatment of acute renal failure, including an Amomi Rotundus Fructus extract or a fraction thereof as an active ingredient.

Another object of the present invention is to provide a functional food composition for the prevention or amelioration of acute renal failure, including the Amomi Rotundus Fructus extract or the fraction thereof as an active ingredient.

Still another object of the present invention is to provide a method for preventing, ameliorating, or treating acute renal failure using the pharmaceutical composition or the functional food composition including the Amomi Rotundus Fructus extract or the fraction thereof as an active ingredient.

Still another object of the present invention is to provide use of the Amomi Rotundus Fructus extract or the fraction thereof in the preparation of the pharmaceutical composition or the functional food composition for the prevention, amelioration or treatment of acute renal failure.

BRIEF DESCRIPTION OF THE DRAWINGS

FIG. 6 is an electrophoresis (A) and a graph (B) showing the result of measuring the p53 expression pattern, which indicates cell death of cisplatin and/or Amomi Rotundus Fructus extract-treated cells according to one Experimental Example of the present invention.

DETAILED DESCRIPTION OF THE PREFERRED EMBODIMENTS

Figure 1A:
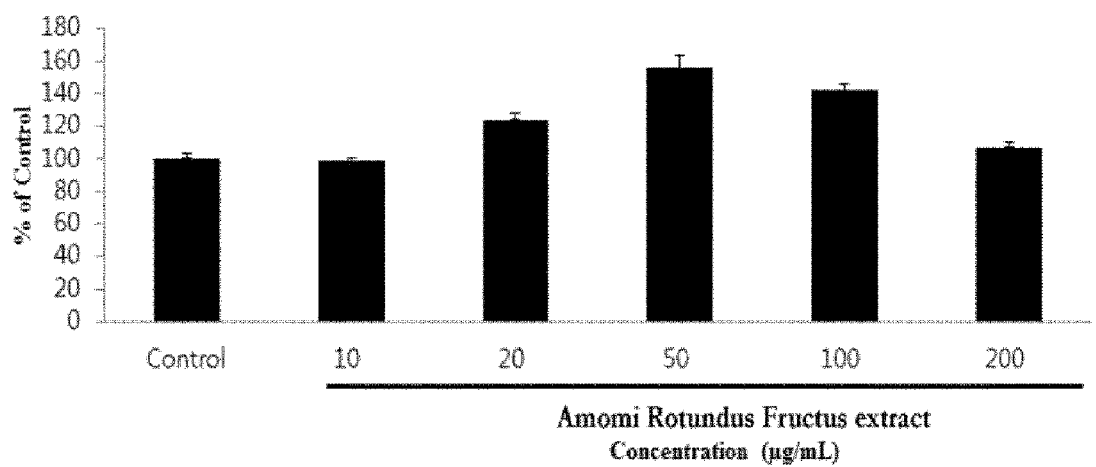
FIG. 1 is a graph showing the result of a cytotoxicity test of Amomi Rotundus Fructus extract or fraction thereof according to one Experimental Example of the present invention (FIG. 1a: Amomi Rotundus Fructus extract, FIG. 1b: the hexane fraction of Amomi Rotundus Fructus, FIG. 1c: the ethyl acetate fraction of Amomi Rotundus Fructus, FIG. 1d: the butanol fraction of Amomi Rotundus Fructus, FIG. 1e: the aqueous fraction of Amomi Rotundus Fructus)

In order to achieve the above objects, the present invention provides a pharmaceutical composition for the prevention or treatment of acute renal failure including an Amomi Rotundus Fructus extract or a fraction thereof as an active ingredient.

As used herein, the term "Amomi Rotundus Fructus" is a Latin name of jave amonum fruit, and means a fruit of *Amomum cadamomum* Linne (Zingiberaceae). Amomi Rotundus Fructus is nearly round shaped and 1 cm to 2 cm in length and 5 mm to mm in diameter. It is externally yellowish-white to yellowish-brown, with three blunt ridges and many longitudinal lines, dented apex, and base with a scar of fruit stalk. The texture of pericarp is thin, light and fibrous, and the interior is longitudinally divided into three loculi by thin membranes, each loculus containing 7 to 10 seeds. The seed is irregularly polyhedral, its dorsal surface is slightly raised, about 3 to 4 mm in diameter, and externally grey brown to dark brown. Under a magnifying glass, Amomi Rotundus Fructus has wrinkled testa and is enveloped in a slightly colored membranaceous aril. Traditionally, Amomi Rotundus Fructus has been known to show effects of relieving the lower chest, warming the stomach, dissipating stagnation, dispersing the abdominal mass, dispersing accumulation, nourishing the lung, relieving hangover, energizing the middle chest, increasing appetite and promoting digestion, promoting the flow of energy in the heart and warming the spleen, and resolving dampness and dispersing the abdominal mass. It acts on the spleen, stomach, and lung, and its nature is known to be non-toxic and mild.

With respect to the objects of the present invention, the Amomi Rotundus Fructus is used for the prevention or treatment of acute renal failure.

The Amomi Rotundus Fructus according to the present invention may be purchased from commercially available sources or collected from or cultured in the wild, but is not limited thereto.

As used herein, the term "extract" means a substance that is isolated and obtained from Amomi Rotundus Fructus, and specifically, a substance that is isolated and obtained using a typical extraction solvent known in the art, for example, water, $c_{1-4}$ alcohol (e.g., methanol, ethanol, butanol, etc.), or a mixture of alcohol and water.

Preferably, the Amomi Rotundus Fructus extract according to the present invention may be a $C_1$-$C_4$ alcohol extract, and more preferably, an ethanol extract.

In a specific embodiment, the Amomi Rotundus Fructus extract was prepared by pulverizing Amomi Rotundus Fructus, adding 7 L of 70% ethanol to 700 g of the pulverized product, carrying out extraction using an ultrasonic extractor for 1 hour three times, carrying out filtration to remove insoluble substances, and then concentrating the resultant at 60° C. under reduced pressure.

As used herein, the term "fraction" means an active fraction that is obtained by fractionating a substance having the desired activity of the present invention from the Amomi Rotundus Fructus extract using a particular solvent.

The solvent used for obtaining the Amomi Rotundus Fructus fraction may be a typical fractionation solvent known in the art, for example, a polar solvent such as water and $C_1$-$C_4$ alcohol (e.g., methanol, ethanol, butanol, etc.), a non-polar solvent such as hexane, ethyl acetate, chloroform, and dichloromethane, or a mixture thereof.

Preferably, the Amomi Rotundus Fructus fraction according to the present invention is a fraction obtained by fractionating the Amomi Rotundus Fructus extract using hexane, ethyl acetate, butanol or water.

The Amomi Rotundus Fructus extract of the present invention or the fraction thereof may also include those obtained by applying an additional purification process. For example, fractions which are obtained by passing the Amomi Rotundus Fructus extract according to the preparation method of the present invention or the fraction thereof through an ultrafiltration membrane with a predetermined molecular weight cut-off value, separating it through various chromatographic (based on size, charge, hydrophobicity or affinity) techniques, and purifying it through various methods are also included in the Amomi Rotundus Fructus extract of the present invention or the fraction thereof.

Further, the Amomi Rotundus Fructus extract of the present invention or the fraction thereof may be prepared in a power form by an additional process such as distillation under reduced pressure and freeze-drying or hot-air drying.

In one specific embodiment, the hexane fraction of Amomi Rotundus Fructus according to the present invention was prepared by suspending the ethanol extract of Amomi Rotundus Fructus in distilled water, and then adding hexane thereto and performing a solvent fractionation three times so as to obtain a hexane fraction, followed by concentration under reduced pressure and freeze-drying (Example 2-1).

In another specific embodiment, the ethyl acetate fraction of Amomi Rotundus Fructus according to the present invention was prepared by adding ethyl acetate to the remaining aqueous fraction after fractionation of the Amomi Rotundus Fructus extract with hexane, and then performing a solvent fractionation three times so as to obtain an ethyl acetate fraction, followed by concentration under reduced pressure and freeze-drying (Example 2-2).

In still another specific embodiment, the butanol fraction of Amomi Rotundus Fructus according to the present invention was prepared by adding butanol to the remaining aqueous fraction after fractionation of the Amomi Rotundus Fructus extract with hexane and ethyl acetate, and then performing a solvent fractionation three times so as to obtain a butanol fraction, followed by concentration under reduced pressure and freeze-drying (Example 2-3).

In still another specific embodiment, the aqueous fraction of Amomi Rotundus Fructus according to the present invention was prepared by concentration under reduced pressure and freeze-drying of the remaining aqueous fraction after fractionation of the Amomi Rotundus Fructus extract with hexane, ethyl acetate and butanol (Example 2-4).

As used herein, the term "acute renal failure" refers to an acute clinical syndrome characterized by rapid decline in renal functions, which is caused by a number of factors such as a reduction in renal blood flow, glomerulonephritis, use of nephrotoxic antibiotics and anticancer agents. The Amomi Rotundus Fructus extract according to the present invention or the fraction thereof can be used for the prevention or treatment of the disease.

On the other hand, cisplatin is a chemotherapeutic drug for malignant tumors including many types of cancers such as testicular, head and neck, ovarian, cervical, non-small cell, or renal cancer (Pala and Dong, 2008; Wang and Lippard, 2005). However, 25-35% of cancer patients experience a significant decline in renal function after the administration of a single dose of cisplatin (Luke et al., 1992), and the most serious side effect in the renal function is a rapid decline in renal function, that is, acute renal failure (Ries and Klastersky, 1986).

As used herein, the term "prevention" refers to all of the actions by which acute renal failure is restrained or retarded by administration of the composition including the Amomi Rotundus Fructus extract or the fraction thereof. As used herein, the term "treatment" refers to all of the actions by which the symptoms of acute renal failure have taken a turn for the better or been cured completely by administration of the composition including the Amomi Rotundus Fructus extract or the fraction thereof.

It is common that levels of ROS (Reactive Oxygen Species), GSH (Glutathione) and p53 inducing and worsening symptoms are measured in the severity test of acute renal failure. ROS is a biochemical index associated with renal injury in various pathological conditions, and the increased ROS level indicates a reduction in GFR. For this reason, high levels of ROS generally indicate the presence of renal disease. Further, GSH or p53 expression level has been used as a basic index for diagnosing acute renal failure induced by an anticancer agent such as cisplatin.

Accordingly, in one specific Experimental Example, the present inventors induced acute renal failure using cisplatin and measured the ROS, GSH and p53 expression levels in order to examine whether the Amomi Rotundus Fructus extract according to the present invention or the fraction thereof shows a prophylactic or therapeutic effect on acute renal failure. As a result, remarkably increased ROS production, reduced GSH content, and increased p53 expression were observed in cisplatin-induced acute renal failure, compared to a non-treated control group. In this regard, when the Amomi Rotundus Fructus extract or the fraction thereof was treated together with cisplatin, ROS production was reduced, GSH content was increased, and p53 expression was suppressed at a level similar to or better than those in the control group. Therefore, it can be seen that the composition including the Amomi Rotundus Fructus extract according to the present invention or the fraction thereof as an active ingredient can be used for the prevention or treatment of acute renal failure.

Figure 2A:
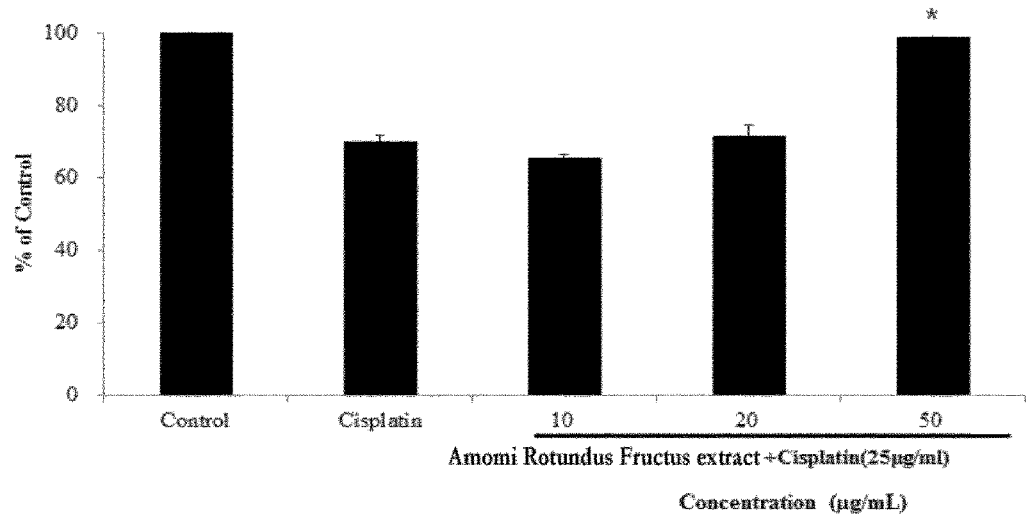
FIG. 2 is a graph showing the result of MTT assay of cisplatin and/or Amomi Rotundus Fructus extract-treated cells according to one Experimental Example of the present invention (FIG. 2A: Amomi Rotundus Fructus extract, FIG. 2b: the hexane fraction of Amomi Rotundus Fructus, FIG. 2c: the ethyl acetate fraction of Amomi Rotundus Fructus, FIG. 2d: the butanol fraction of Amomi Rotundus Fructus, FIG. 2e: aqueous fraction of Amomi Rotundus Fructus)
Figure 2B:
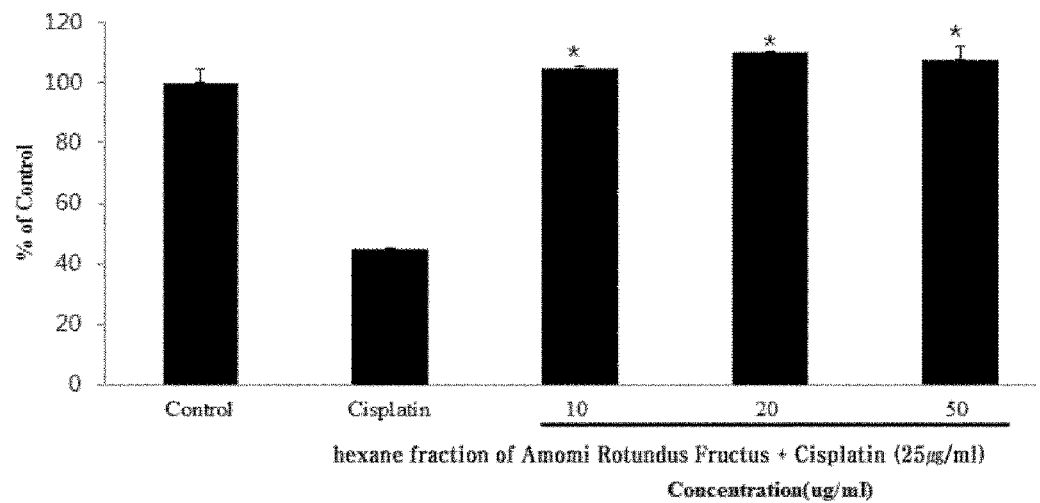
Figure 2C:
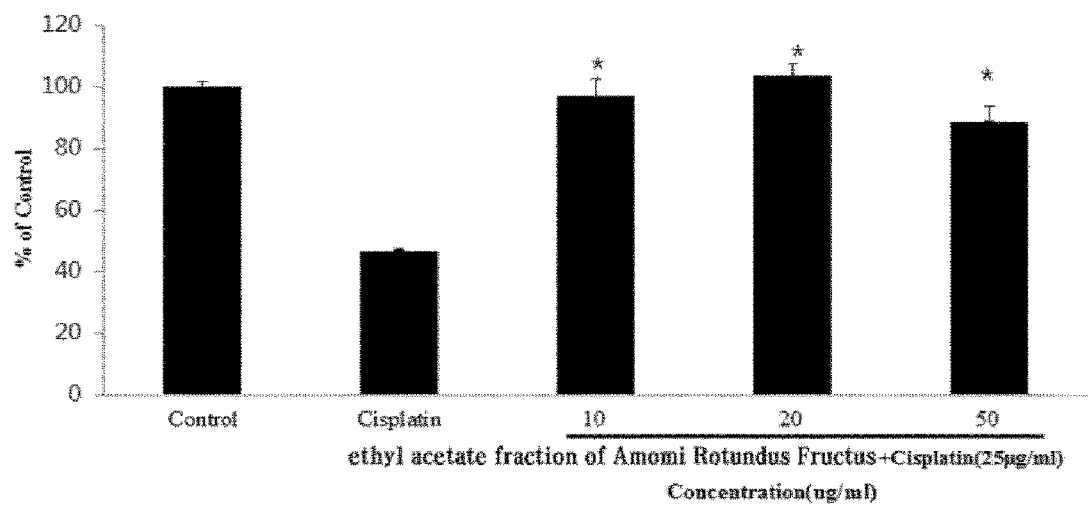
Figure 2D:
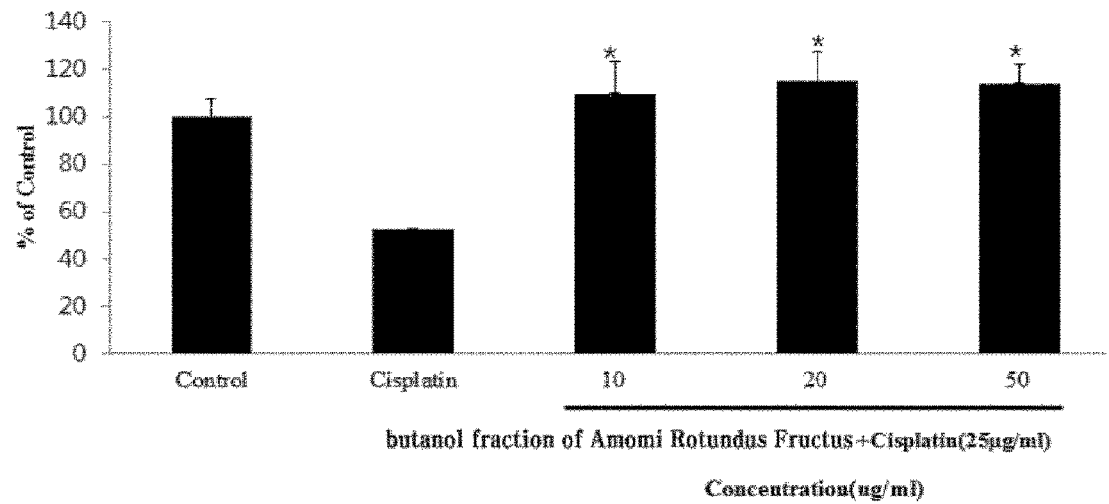
Figure 2E:
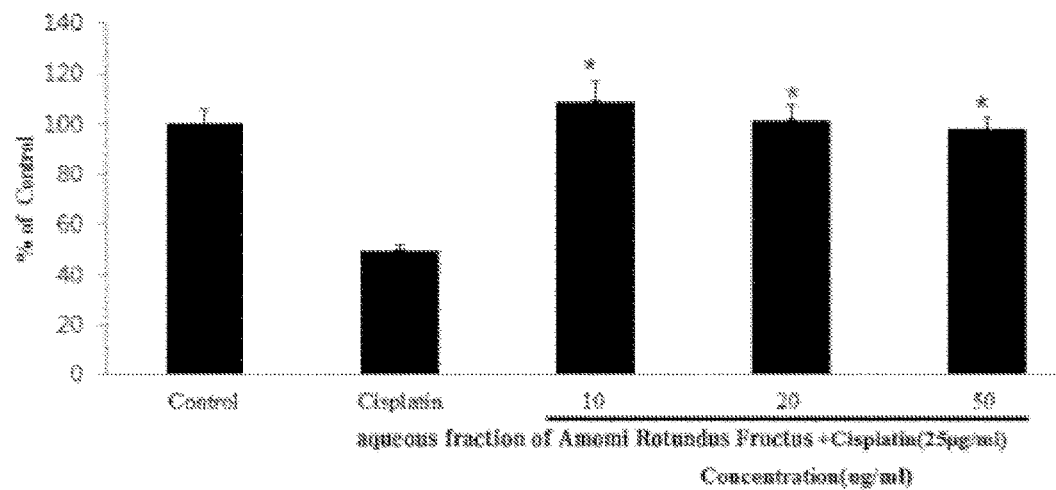

In another specific Experimental Example, treatment of renal cells with cisplatin remarkably reduced cell viability, whereas co-treatment of the Amomi Rotundus Fructus extract or the fraction thereof with cisplatin increased cell viability in a concentration-dependent manner, indicating that the Amomi Rotundus Fructus extract of the present invention or the fraction thereof is able to effectively protect renal cells from cisplatin cytotoxicity (FIGS. 2a to 2e).

In another aspect, the present invention provides a method for preventing or treating acute renal failure by administering the pharmaceutical composition including the Amomi Rotundus Fructus extract or the fraction thereof as an active ingredient to a subject including human in need thereof.

As used herein, the term "subject" means all animals including humans who have already had acute renal failure or have a possibility of having acute renal failure. The above disease can be effectively prevented and treated by administering the composition of the present invention to the subject.

The composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level may be determined depending on a subject's type, severity of the disease, the subject's age and sex, activity of the drug, sensitivity to the drug, administration time, administration route, excretion rate, duration of treatment, drugs used in combination with the composition, and other factors known in the medical field. The composition of the present invention may be administered alone or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, this amount can be easily determined by a person skilled in the art.

The preferred administration dose of the pharmaceutical composition of the present invention may be 0.1 mg/kg/day to 1,000 mg/kg/day.

The composition of the present invention may include a pharmaceutically acceptable carrier, excipient, or diluent, in addition to the Amomi Rotundus Fructus extract or the fraction thereof. Examples of the carrier, excipient, and diluent may include lactose, dextrose, sucrose, sorbitol, mannitol, xylitol, erythritol, maltitol, starch, *acacia* rubber, alginate, gelatin, calcium phosphate, calcium silicate, cellulose, methyl cellulose, microcrystalline cellulose, polyvinylpyrrolidone, water, methylhydroxy benzoate, propylhydroxy benzoate, talc, magnesium stearate and mineral oil, but are not limited thereto.

According to the conventional methods, the composition of the present invention may be formulated into an oral preparation such as a powder, a granule, a tablet, a capsule, a suspension, an emulsion, a syrup, or an aerosol, an external preparation, suppository, or a sterilized injectable solution. In detail, such preparations may be prepared using diluents or excipients ordinarily employed, such as a filler, an extender, a binder, a wetting agent, a disintegrating agent, and a surfactant. Examples of the solid preparation for oral administration include a tablet, a pill, a powder, a granule, and a capsule, but are not limited thereto. The solid preparation may be prepared by mixing with at least one excipient such as starch, calcium carbonate, sucrose, lactose, or gelatin. Further, in addition to the excipients, lubricants such as magnesium stearate and talc may be used. It may be prepared by adding various excipients such as a wetting agent, a sweetener, a flavor, or a preservative, in addition to a liquid for internal use and liquid paraffin. Examples of the preparation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, or an injectable ester such as ethyloleate may be used. As a suppository base, witepsol, macrogol, tween 61, cacao butter, lauric butter, glycerogelatin or the like may be used.

The composition of the present invention may be administered via an oral route or a parenteral route (e.g., intravenously, subcutaneously, intraperitoneally, or topically) according to the desired method, and the administration dose may be properly determined by those skilled in the art, depending on a patient's condition and body weight, severity of the disease, type of the drug, administration route and time.

In still another aspect, the present invention provides a functional food composition for the prevention or amelioration of acute renal failure including the Amomi Rotundus Fructus extract or the fraction thereof as an active ingredient. The Amomi Rotundus Fructus extract, the fraction thereof, and acute renal failure are the same as described above.

As used herein, the term "amelioration" refers to all of the actions by which the parameters associated with conditions under treatment, for example, the symptoms are lessened.

The functional food may include various nutrients, vitamins, minerals (electrolyte), flavoring agents such as synthetic flavoring agents and natural flavoring agents, coloring agents and improving agents (cheese, chocolate, etc.), pectic acid and salts thereof, alginic acid and salts thereof, organic acids, protective colloidal thickening agents, pH controlling agents, stabilizing agents, preservatives, glycerin, alcohol, carbonizing agents as used in carbonated beverages, etc. Additionally, the functional food may include fruit flesh for the preparation of natural fruit juices, fruit juice beverages and vegetable juices. These components may be used alone or in combination. In addition, the functional food may be any one of meats, sausages, bread, chocolate, candies, snack, confectionery, pizza, noodles, gums, ice creams, soups, beverages, teas, functional water, drinks, alcoholic beverages and multi-vitamin preparations.

Further, the functional food may further include a food additive, and whether or not the functional food is suitable as a food additive material is determined based on a standard and criteria relating to a relevant item according to general rules disclosed in Korean Food Additives Codex and a general test method that have been approved by Ministry of Food and Drug Safety (Korea) as long as other rules is not provided.

The items disclosed in such "Korean Food Additives Codex" may include, for example, a chemically synthetic composite, such as ketones, glycine, calcium citrate, nicotinic acid, and cinnamic acid; a natural additive material, such as persimmon color, licorice extract, microcrystalline cellulose, and guar gum; and mixed formulations, such as sodium L-glutamate formulation, alkali agents for noodles, preservative formulation, and tar color formulation.

In the preparation of the functional food, the content of the extract according to the present invention which is added to foods including drinks may be properly adjusted, if necessary.

In still another aspect, the present invention provides a method for preventing or ameliorating acute renal failure including the step of administering the functional food composition to a subject.

In still another aspect, the present invention provides use of the Amomi Rotundus Fructus extract or the fraction thereof in the preparation of the pharmaceutical composition or the functional food composition for the prevention, amelioration or treatment of acute renal failure.

The pharmaceutical composition for the prevention or treatment of acute renal failure, and the functional food composition for prevention or amelioration of acute renal failure are the same as described above.

Hereinafter, the preferred Examples are provided for better understanding. However, the following Examples are for illustrative purposes only, and the invention is not intended to be limited by these Examples.

Example 1: Preparation of Amomi Rotundus Fructus Extract

Commercially available Amomi Rotundus Fructus was purchased and pulverized, and 3 L of 70% ethanol was added to 300 g of the pulverized product, followed by ultrasonic extraction using an ultrasonic extractor for 1 hour three times. The liquid extract was filtered using Whatman (46 cm×57 cm) filter paper to remove insoluble materials, and concentrated under reduced pressure at 60° C. using a concentrator equipped with a cooling condenser. To completely remove the solvent from the extract concentrated under reduced pressure, 100 mL of purified water was added and suspended, and thus 14.60 g of the extract was obtained using a freeze dryer (yield: 4.87%).

Example 2: Preparation of Fractions of Amomi Rotundus Fructus Extract 2-1. Preparation of the Hexane Fraction from Amomi Rotundus Fructus 14 g of the Amomi Rotundus Fructus extract of Example 1 was suspended in 0.4 L of distilled water, and then 0.4 L of hexane was added to carry out a solvent fractionation three times. A hexane fraction thus obtained was concentrated under reduced pressure, and freeze-dried to obtain 1.54 g of hexane fraction (yield: 10.97%).

2-2. Preparation of the ethyl acetate fraction from Amomi Rotundus Fructus 0.4 L of ethyl acetate was added to the remaining aqueous fraction after hexane fractionation of Example 2-1, and then a solvent fractionation was carried out three times. An ethyl acetate fraction thus obtained was concentrated under reduced pressure, and then freeze-dried to obtain 0.99 g of ethyl acetate fraction (yield: 7.08%).

2-3. Preparation of the Butanol Fraction from Amomi Rotundus Fructus 0.4 L of butanol was added to the remaining aqueous fraction after ethyl acetate fractionation of Example 2-2, and then a solvent fractionation was carried out three times. A butanol fraction thus obtained was concentrated under reduced pressure, and then freeze-dried to obtain 0.93 g of butanol fraction (yield: 6.65%).

2-4. Preparation of the aqueous fraction from Amomi Rotundus Fructus

The remaining aqueous fraction after butanol fractionation of Example 2-3 was concentrated under reduced pressure, and then freeze-dried to obtain 7.3 g of aqueous fraction (yield: 52.14%).

Experimental Example 1: Cytotoxicity Test

Figure 1B:
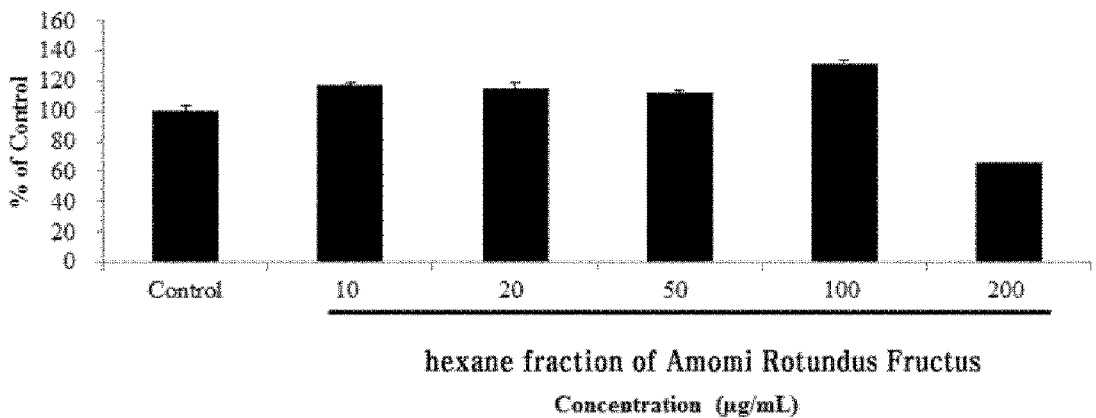
Figure 1C:
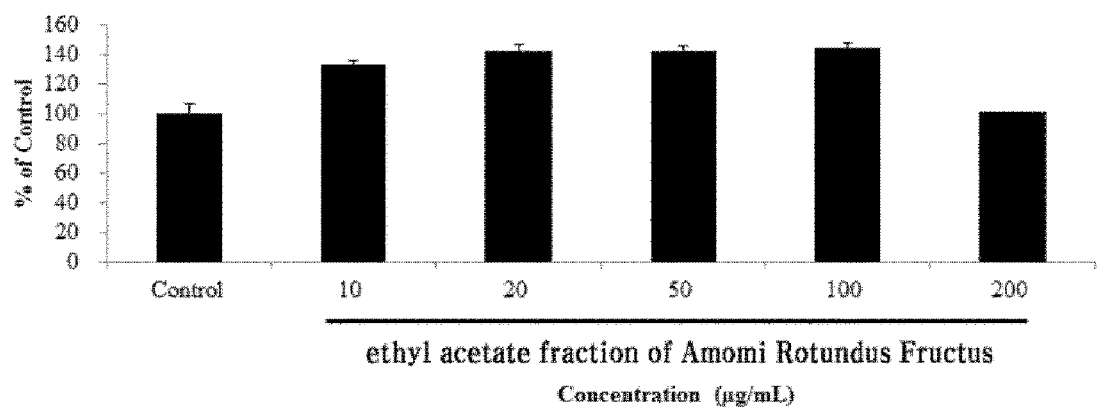
Figure 1D:
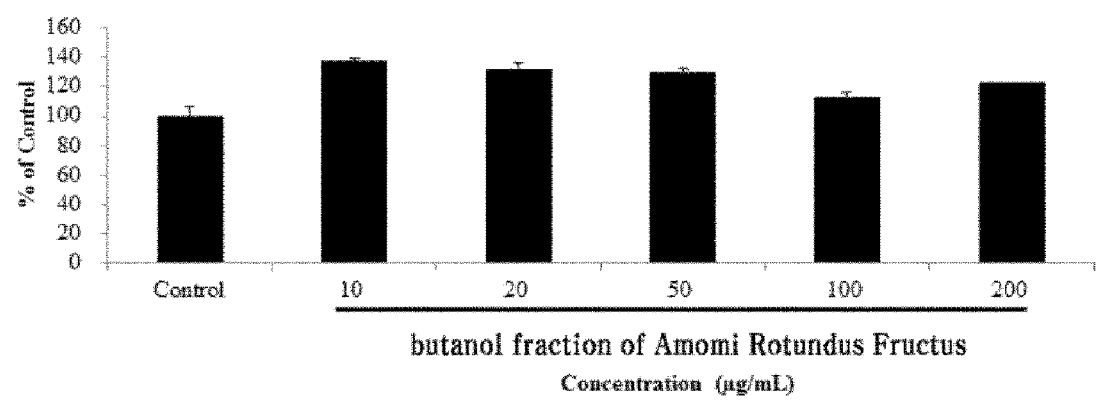
Figure 1E:
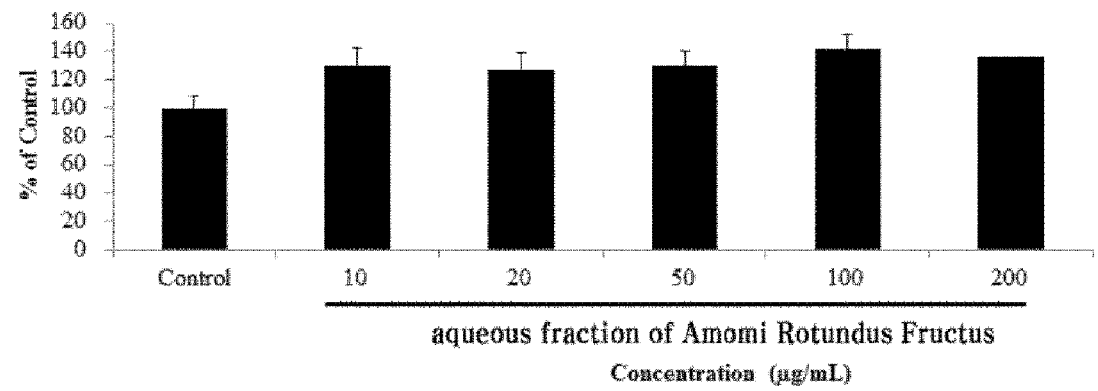

In order to examine cytotoxicity of the Amomi Rotundus Fructus extract prepared in Example 1 and the fractions thereof prepared in Example 2, the following experiment was performed. First, porcine renal epithelial cells were seeded at a density of $1\times10^4$ cells per well of 96-well plate, and then the cells were treated with the Amomi Rotundus Fructus extract prepared by the method of Example 1 or the fractions thereof at a concentration of 10, 20, 50, 100, 200 μg/ml (treatment concentration: 20, 40, 100, 200, 400 μg/ml). The drug treatment dose was 50 μl, and after culture for 24 hrs, final treatment was carried out at a final PBS concentration of 1% (treatment concentration: 2%), Stock: 20 mg/ml (in PBS: 100 mg/ml dilution) and then absorbance at 450 nm was measured and calculated, and the mean value of wells was used. The measured values were examined by comparing the experimental results according to concentration for 24 hours, and the results are shown in FIG. 1.

As shown in FIGS. 1a to 1e, it was found that the Amomi Rotundus Fructus extract or the fraction thereof has no cytotoxicity.

Experimental Example 2: In Vitro Efficacy Test on Acute Renal Failure

<1> MTT Assay

To measure cell viability of renal cells by the Amomi Rotundus Fructus extract and the fraction thereof, MTT assay was performed. First, renal cells were seeded at a density of $1\times10^4$ cells per well of 96-well plate. After 24 hours, the cells were treated with each 50 μg thereof which was prepared by dilution at three final concentrations (50, 100, 200 μg/ml). After 2 hours, cisplatin was treated at a final concentration of 25 μg/ml, and cells were cultured for 24 hours. After 24 hours, 10 μl of the assay reagent of EZ-Cytox Cell Viability assay kit was added to each well using a Micro multi Pipette, taking care to introduce no bubbles, and reaction was allowed for 4 hours under basic culture conditions. Absorbance at 450 nm was measured. $p<0.005$ was considered statistically significant.

As shown in FIGS. 2a to 2e, it was found that cell viability was remarkably reduced by cisplatin treatment, based on 100% cell viability of the control group, but recovered by treatment of the Amomi Rotundus Fructus extract or the fraction thereof.

Figure 3A:
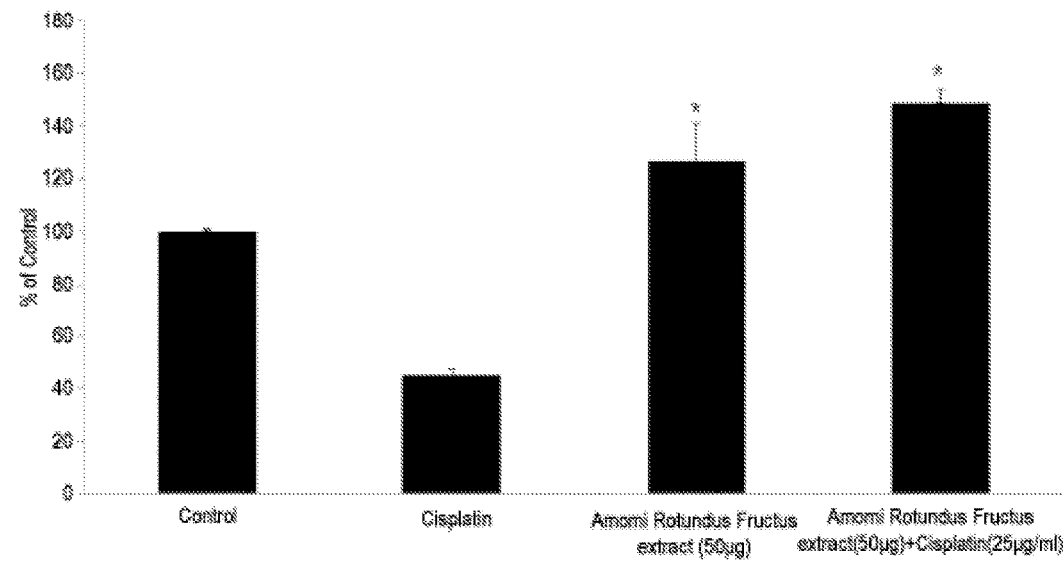
FIG. 3 is a graph showing the result of cell viability of Amomi Rotundus Fructus extract and cisplatin-treated cells according to one Experimental Example of the present invention, compared with the control group (FIG. 3a: Amomi Rotundus Fructus extract, FIG. 3b: the hexane fraction of Amomi Rotundus Fructus, FIG. 3c: the ethyl acetate fraction of Amomi Rotundus Fructus, FIG. 3d: the butanol fraction of Amomi Rotundus Fructus, FIG. 3e: the aqueous fraction of Amomi Rotundus Fructus)
Figure 3B:
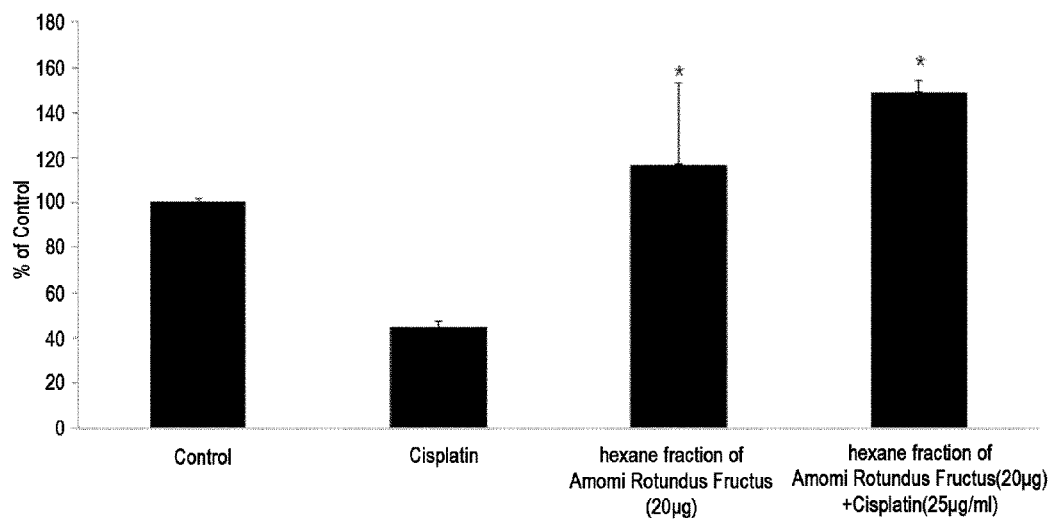
Figure 3C:
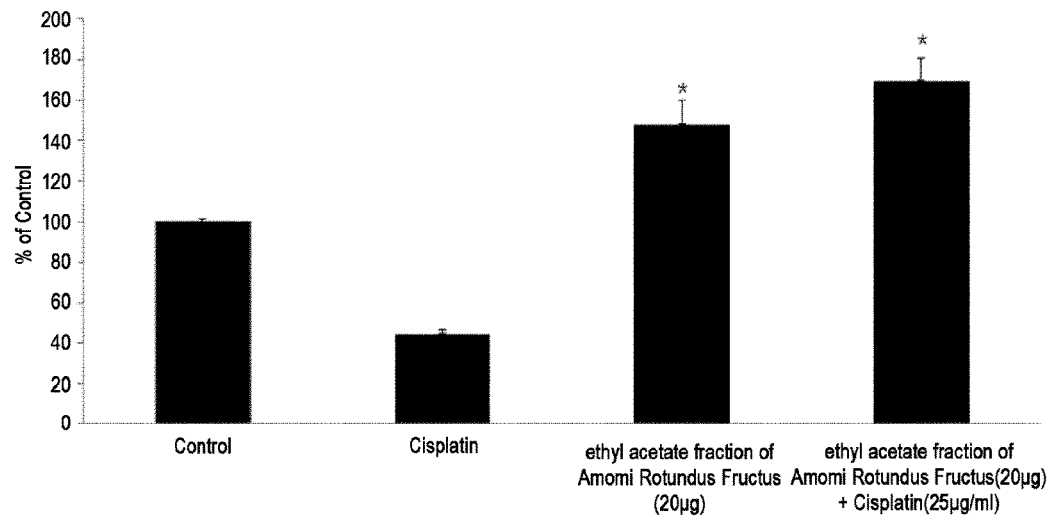
Figure 3D:
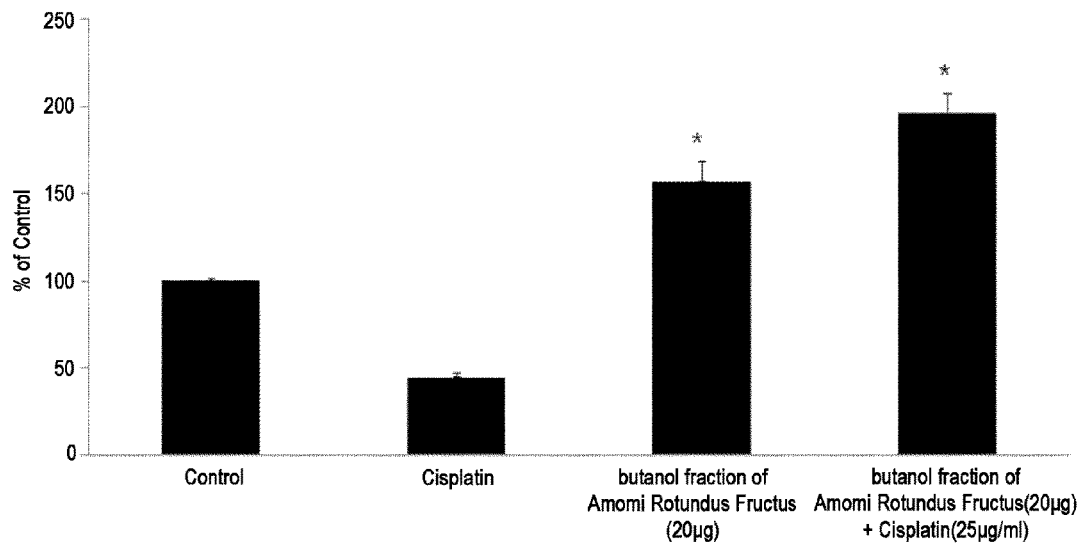
Figure 3E:
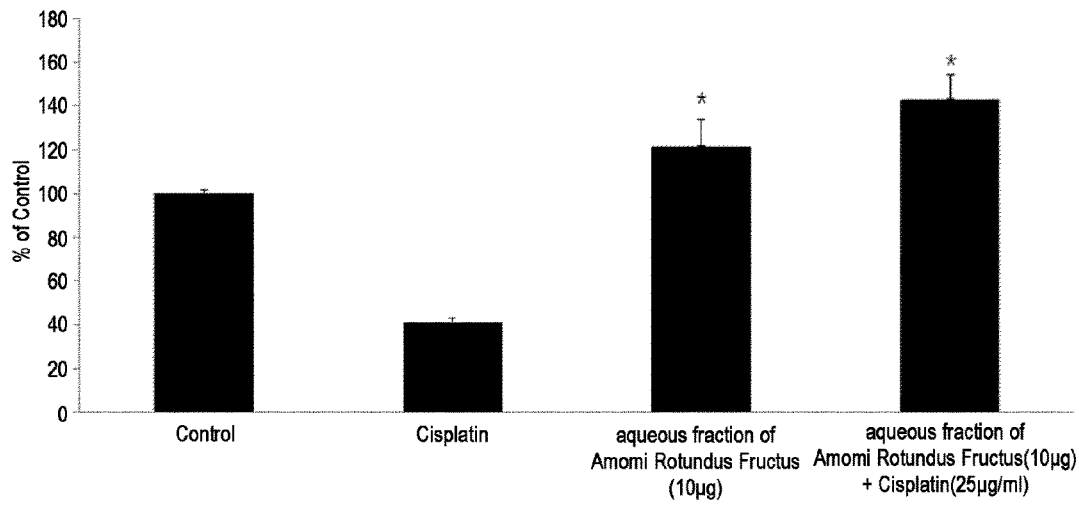

As shown in FIGS. 3a to 3e, it was found that single treatment of the Amomi Rotundus Fructus extract or the fraction thereof showed 100% cell activity or higher, based on 100% cell activity of the control group, indicating that the Amomi Rotundus Fructus extract or the fraction thereof activates cells. In contrast, it was found that single treatment of cisplatin showed about 40% cell activity or less, indicating its cytotoxicity. In this regard, co-treatment of cisplatin with the Amomi Rotundus Fructus extract or the fraction thereof showed excellent cell activity identical or similar to that of the control group or single treatment of the Amomi Rotundus Fructus extract.

<2> Measurement of ROS Generation

In order to measure antioxidant effect of the Amomi Rotundus Fructus extract and the fraction thereof in renal cells, ROS generation test was performed. First, renal cells were seeded at a density of $1\times10^5$ cells per well of 96-well plate. After 24 hours, the cells were pre-treated with 100 μg of the Amomi Rotundus Fructus extract. 2 hours after treatment, cisplatin was treated at a final concentration of 25 μg/ml, followed by culture for 24 hours. DCF-DA dissolved in PBS was treated in the dark according to the treatment concentration of DCF-DA and the reaction time which were determined by historical data and preliminary experiment, and reaction was allowed for 5 hours under basic culture conditions. At the time point of 0, 4, 8, 12, 16, 20, 24 hr, end-point fluorescence wavelength at Ex: 485 nm and Em: 528 nm was measured at S=50.

Figure 4A:
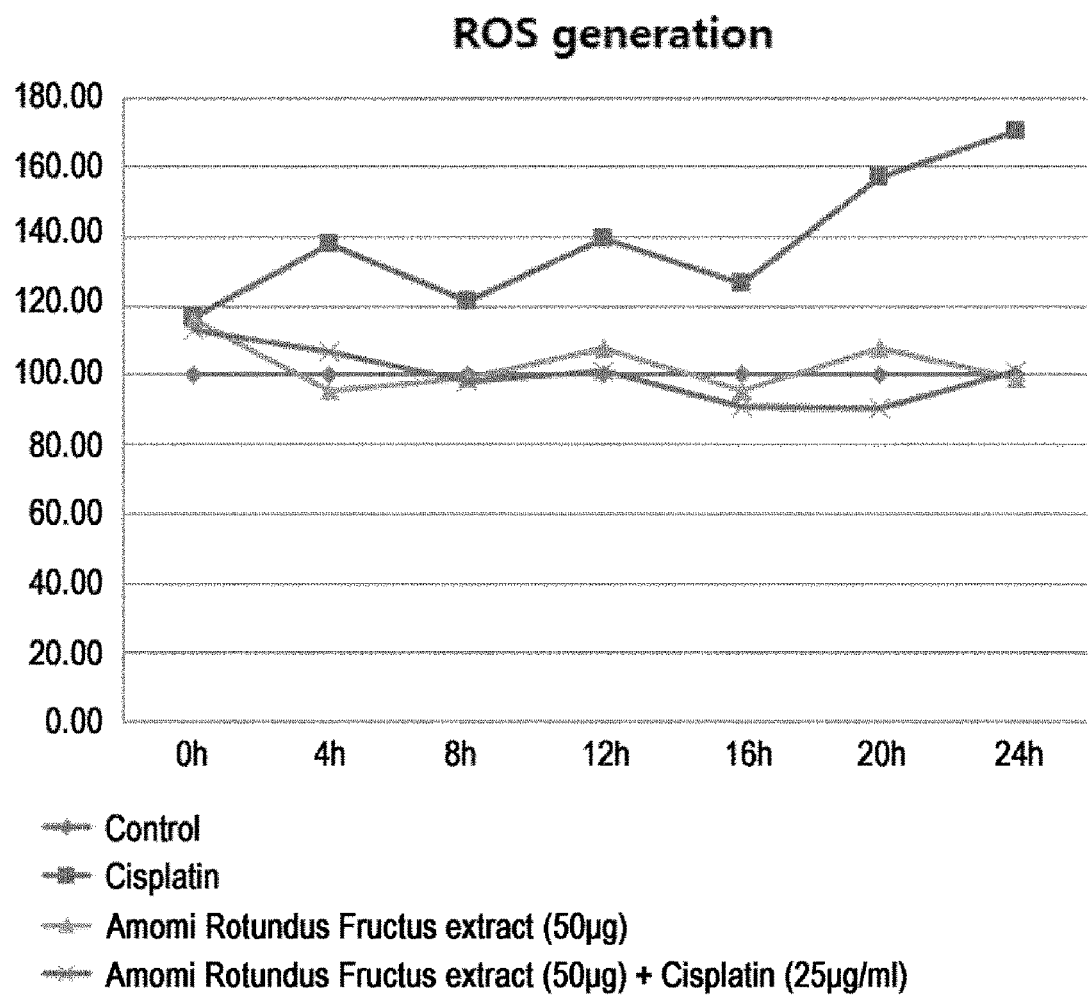
FIG. 4 is a graph showing the result of measuring the antioxidant activity index, ROS generation of cisplatin and/ or Amomi Rotundus Fructus extract-treated cells according to one Experimental Example of the present invention (FIG. 4a: Amomi Rotundus Fructus extract, FIG. 4b: the hexane fraction of Amomi Rotundus Fructus, FIG. 4c: the ethyl acetate fraction of Amomi Rotundus Fructus, FIG. 4d: the butanol fraction of Amomi Rotundus Fructus, FIG. 4e: the aqueous fraction of Amomi Rotundus Fructus)
Figure 4B:
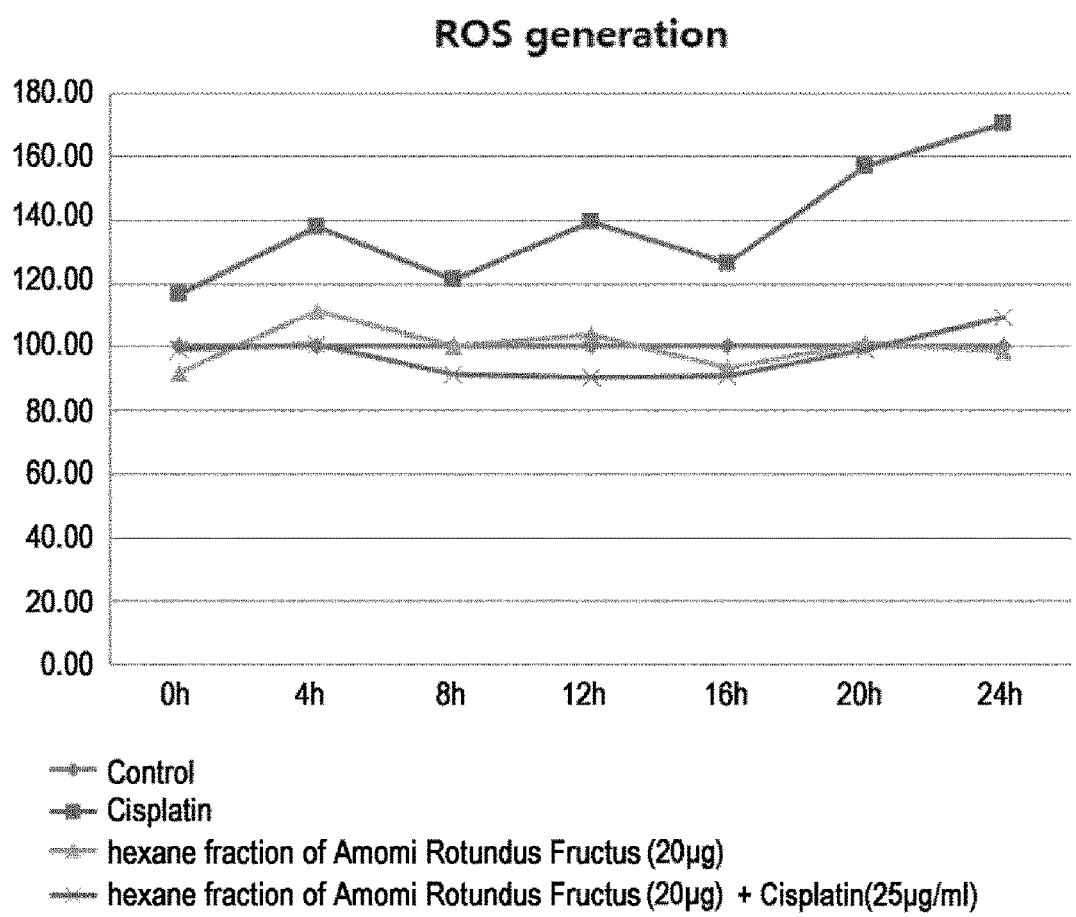
Figure 4C:
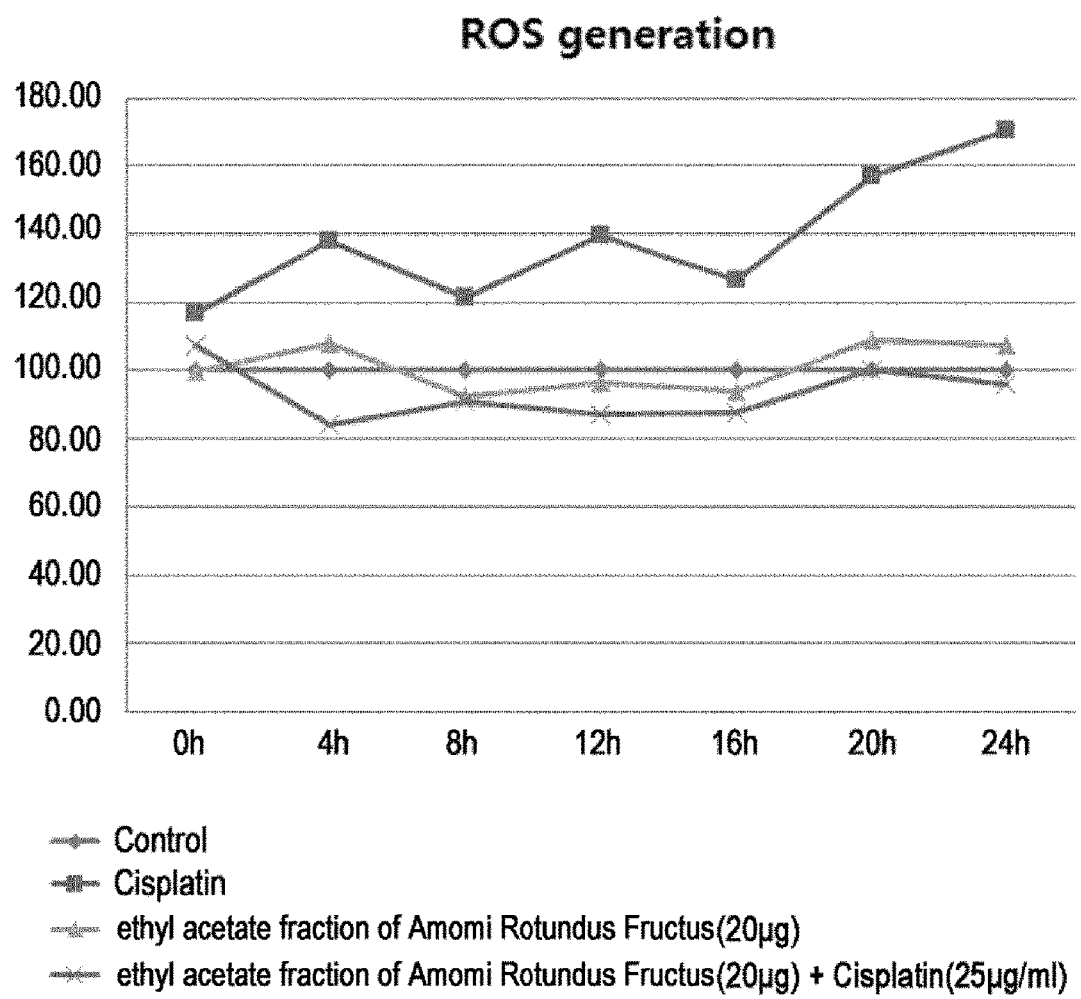
Figure 4D:
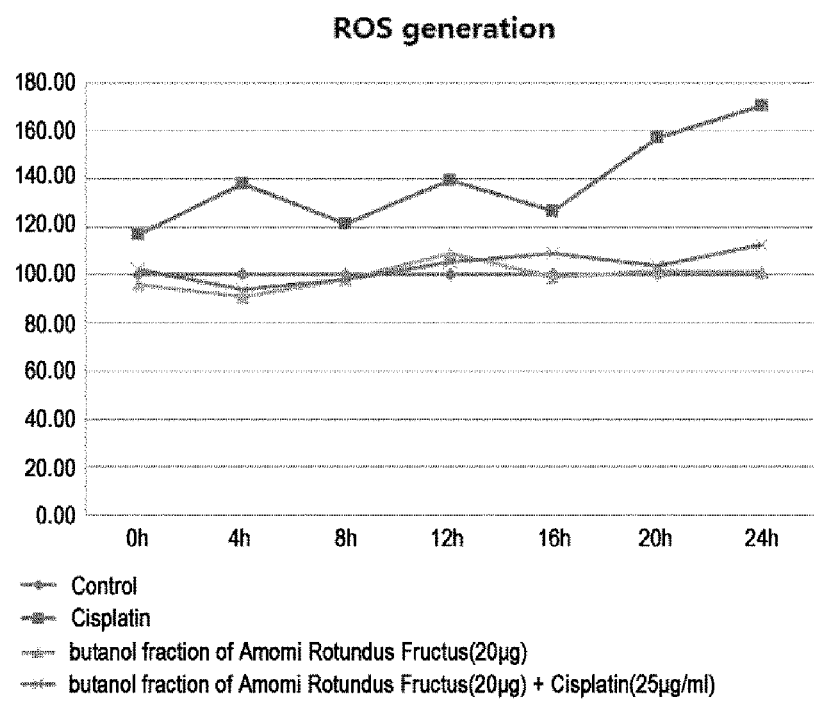
Figure 4E:
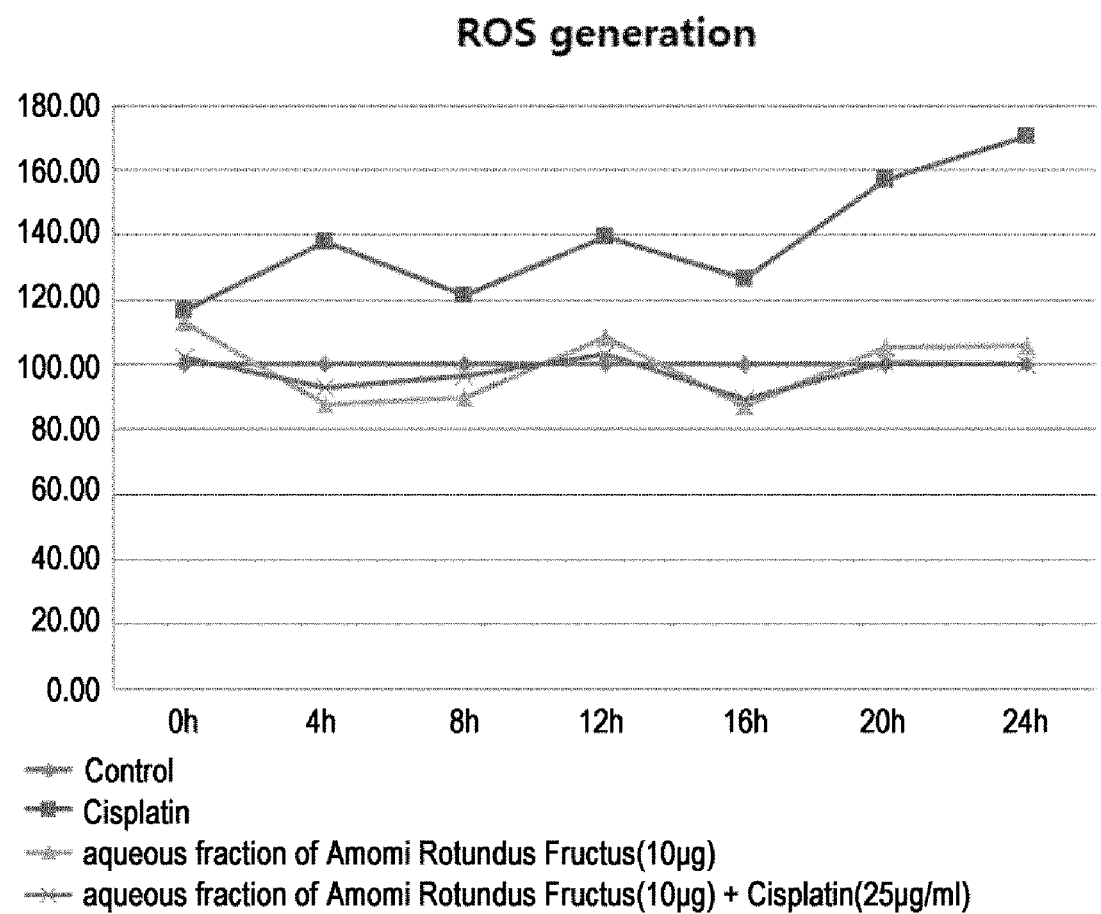

As shown in FIGS. 4a to 4e, single treatment of cisplatin showed about 170% ROS generation or higher after 24 hours, based on 100% ROS generation of the control group, indicating remarkable nephrotoxicity. In this regard, co-treatment of cisplatin with the Amomi Rotundus Fructus extract or the fraction thereof showed a reduction in ROS generation, which was identical to or higher than that of single treatment of the Amomi Rotundus Fructus extract.

Therefore, when a nephrotoxic agent such as cisplatin is treated together with the Amomi Rotundus Fructus extract or the fraction thereof, cisplatin-induced ROS generation can be remarkably reduced to effectively inhibit nephrotoxicity.

<3> Measurement of GSH Content

Because GSH level is known as an index to evaluate a cell-protecting effect on drug-induced cellular injury, GSH level was measured to examine the cell-protecting effect of the Amomi Rotundus Fructus extract or the fraction thereof against cisplatin. The GSH levels were determined by monochlorobimane, and experiments for measuring GSH content were performed using the kidney tissues with reference to the conventional method of Fernandez-Checa and Kaplowitz. The number of cells, in which GSH is detectable, was determined by historical data and preliminary experiment, and $2 \times 10^6$ cells were seeded to each well of culture plate. After culture for 24 hours, the dilution fold of the final concentration of the drug determined as an active drug was considered and calculated, based on the results of MTT Assay and crystal violet Assay. The drug was diluted and pre-treated, and cisplatin was added at a final concentration of μg/ml at 2 hours after drug treatment, followed by culture for 24 hours. Cells were harvested using 0.25% Trypsin-EDTA, and then centrifuged at 1,200 rpm for 3 minutes. Cold buffer was added to the cell pellet, followed by sonication for 30 seconds. Centrifugation was carried out at 10,000 rpm for 15 minutes, and then the supernatant was collected and used for BCA protein quantification. 1 g/ml of MPA diluted in D.W was added to the supernatant at a volume ratio of 4:1, followed by immediately vortexing. Centrifugation was carried out at 10,000 rpm for 15 minutes, and the deprotenized supernatant was collected and prepared as a sample for GSH assay. The remainder was stored at −20° C. For measurement, first, GSH Standard (L-Glutathione reduced, Sigma-Aldrich) was diluted in D.W at a concentration of 0, 0.2, 0.4, 0.8, 1.2, 1.6, and 2.0 μg/ml, and repeated twice or more times, and then each 20 μl thereof was added to renal cells in 96-well black plates. The same amount of the sample was added repeatedly twice or more times, and then 180 μl of buffer was added to each well. 10 μl of OPA (Phthaldialdehyde, Sigma-Aldrich) which was diluted in anhydrous methanol at a concentration of 1 mg/ml was added to each well, and allowed to react at room temperature for 15 minutes. End-point fluorescence wavelength at Ex: 360 nm and Em: 460 nm was measured at S=70. Data of the experimental results were analyzed using Microsoft Excel program, and post-test analysis using Bonferroni multiple comparison test was performed to investigate the differences between the groups. $p<0.001$ was considered statistically significant.

Figure 5A:
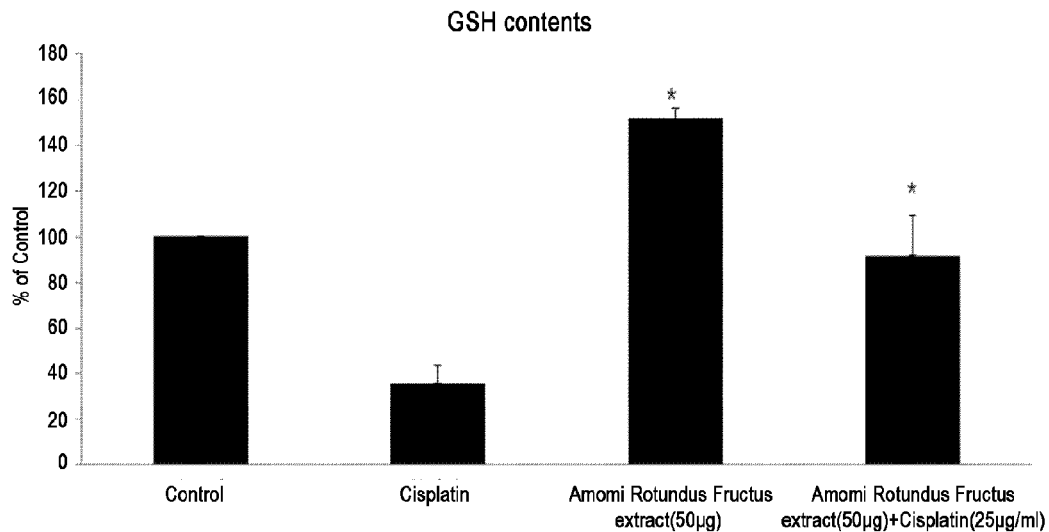
FIG. 5 is a graph showing the result of measuring the GSH content, which indicates a cell-protecting effect on cell injury of cisplatin and/or Amomi Rotundus Fructus extract-treated cells according to one Experimental Example of the present invention (FIG. 5a: Amomi Rotundus Fructus extract, FIG. 5b: the hexane fraction of Amomi Rotundus Fructus, FIG. 5c: the ethyl acetate fraction Amomi Rotundus Fructus, FIG. 5d: the butanol fraction of Amomi Rotundus Fructus, FIG. 5e: the aqueous fraction of Amomi Rotundus Fructus)
Figure 5B:
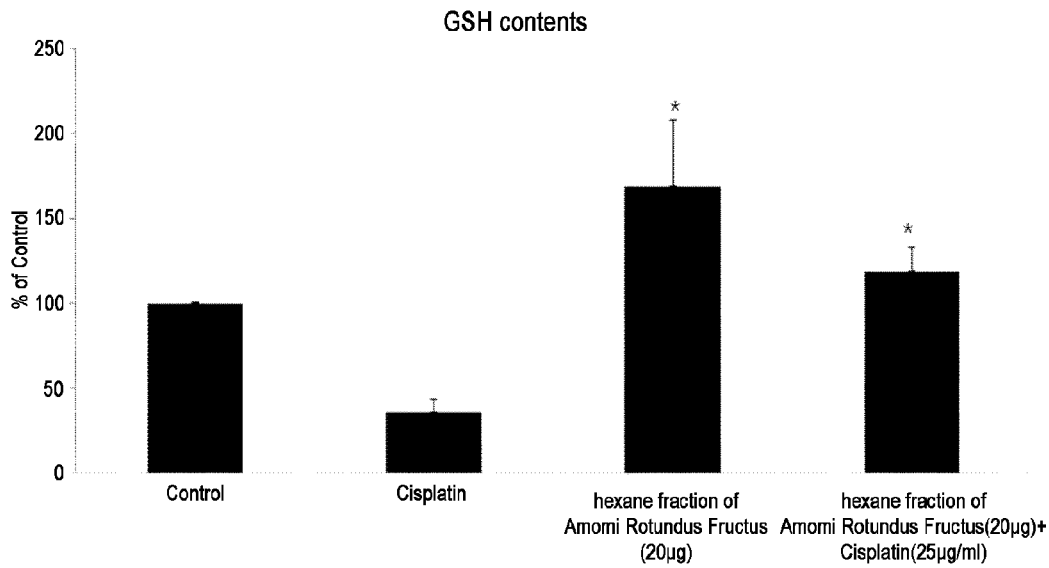
Figure 5C:
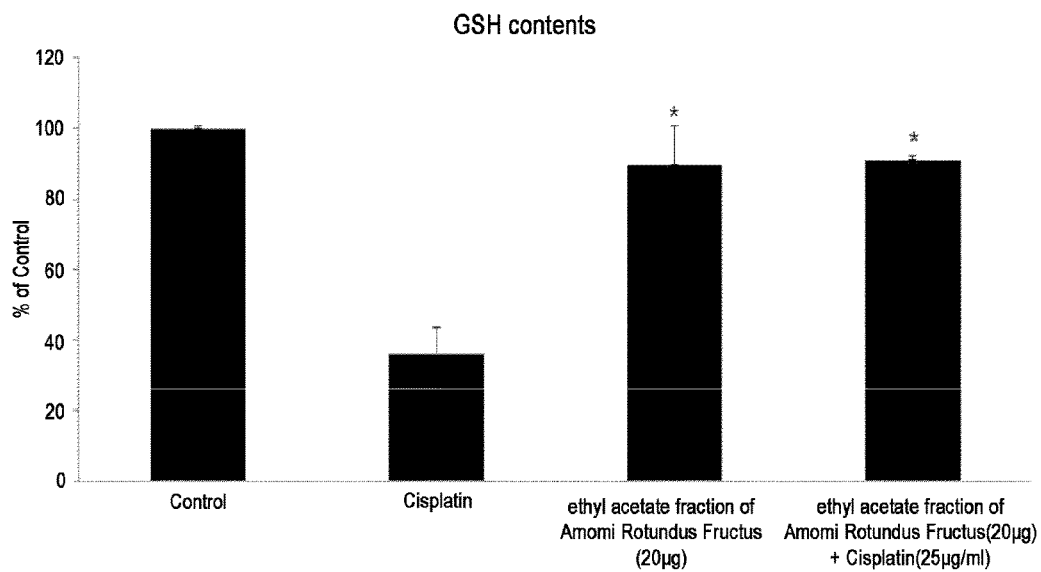
Figure 5D:
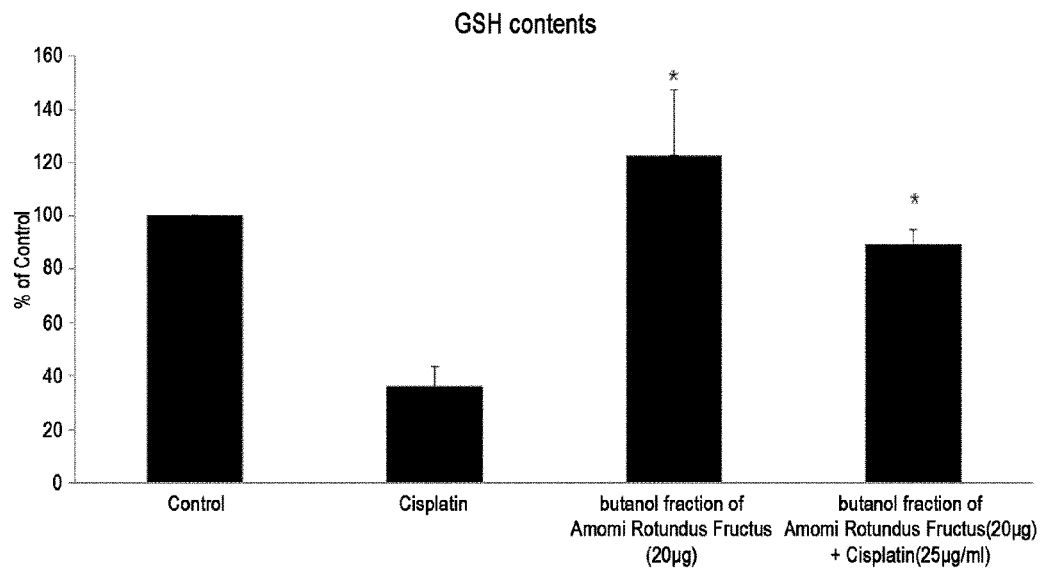
Figure 5E:
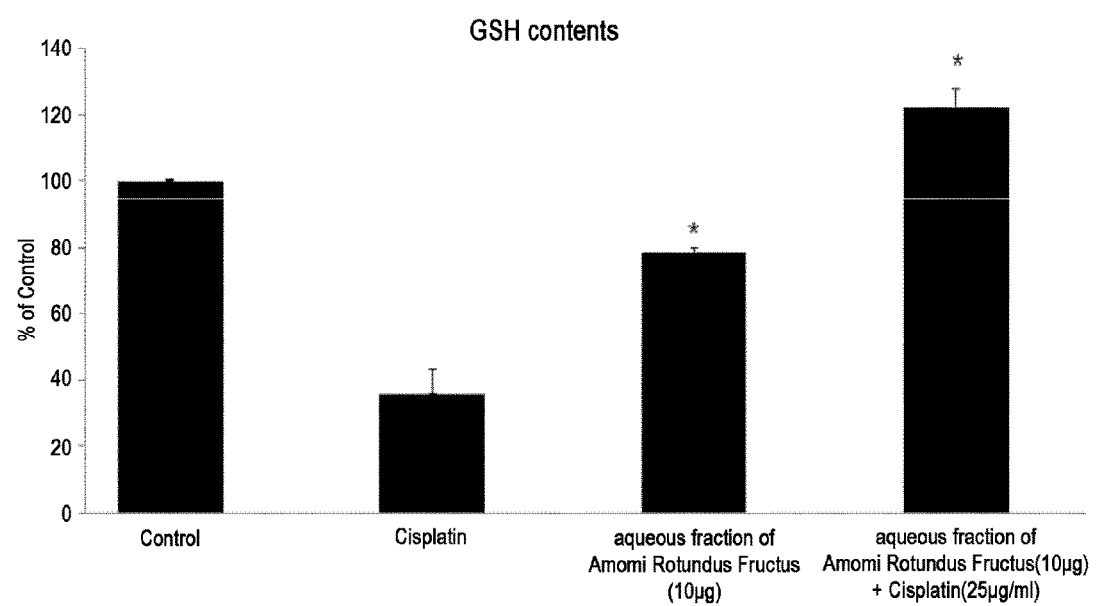

As shown in FIGS. 5a to 5e, the GSH content was reduced by single treatment of cisplatin, but recovered at the level equivalent to or higher than that of the normal control group by co-treatment of cisplatin with the Amomi Rotundus Fructus extract or the fraction thereof. Therefore, it can be seen that the Amomi Rotundus Fructus extract or the fraction thereof effectively restores cisplatin-induced cell injury and has excellent cell-protecting effects.

<4> Examination of p53 Expression Pattern

Cells treated with Amomi Rotundus Fructus extract and/or cisplatin were harvested, and RIPA buffer was added thereto, followed by sonication for cell lysis. Centrifugation was performed at 15,000 rpm for 15 minutes, and the supernatant was obtained, and subjected to protein quantification by BCA assay. The protein was loaded at an amount of 20 μg/10 μl in each well, and 12% SDS-PAGE polyacrylamide gel electrophoresis was performed, and transferred to a nitrocellulose membrane. The membrane was blocked with 5% Skim milk-TBST, and then treated with primary antibody (anti-p53/dilution-1:300). p53 was detected with HRP conjugated anti-mouse IgG (dilution-1:5000) and immune reaction was visualized by ECL. The measurement results are shown as Mean±S.E.M. (standard error of mean) in FIG. 6. Data of the experimental results were analyzed using Microsoft Excel program, and post-test analysis using Bonferroni multiple comparison test was performed to investigate the differences between the groups. $p<0.001$ was considered statistically significant, and expressed as *; $p<0.001$ to compare with cisplatin.

As shown in FIG. 6, the p53 expression level was remarkably increased by single treatment of cisplatin, whereas the p53 expression level by the co-treatment of cisplatin with the Amomi Rotundus Fructus extract was lower than that of the normal control group.

EFFECT OF THE INVENTION

The Amomi Rotundus Fructus extract or the fraction thereof according to the present invention exhibits the effects of reducing ROS generation, increasing GSH content, and reducing p53 expression in an acute renal failure cell model, and therefore, it can be used for the prevention or treatment of acute renal failure.

What is claimed is:

1. A method for treating acute renal failure, comprising administering a pharmaceutical composition to a subject in need thereof, wherein the pharmaceutical composition comprises an effective amount of a C1-C4 alcoholic or aqueous C1-C4 alcoholic Amomi Rotundus Fructus extract or a fraction thereof as an active ingredient, wherein the fraction of the Amomi Rotundus Fructus extract is obtained by fractionating the Amomi Rotundus Fructus extract with hexane, ethyl acetate, butanol, water or a mixed solvent thereof.

2. The method according to claim 1, wherein the acute renal failure is caused by an anticancer agent.

3. The method according to claim 2, wherein the anticancer agent is cisplatin.

4. The method according to claim 1, wherein the Amomi Rotundus Fructus extract is obtained by extracting Amomi Rotundus Fructus with ethanol.

5. A method for ameliorating acute renal failure, comprising administering a functional food composition to a subject in need thereof, wherein the functional food composition comprises an effective amount of a C1-C4 alcoholic or aqueous C1-C4 alcoholic Amomi Rotundus Fructus extract or a fraction thereof as an active ingredient, wherein the fraction of the Amomi Rotundus Fructus extract is obtained by fractionating the Amomi Rotundus Fructus extract with hexane, ethyl acetate, butanol, water or a mixed solvent thereof.

6. The method according to claim 5, wherein the acute renal failure is caused by an anticancer agent.

7. The method according to claim 6, wherein the anticancer agent is cisplatin.

8. The method according to claim 5, wherein the Amomi Rotundus Fructus extract is obtained by extracting Amomi Rotundus Fructus with ethanol.

9. The method according to claim 5, wherein the fraction of the Amomi Rotundus Fructus extract is obtained by fractionating the Amomi Rotundus Fructus extract with hexane, ethyl acetate, butanol, water or a mixed solvent thereof.

* * * * *